United States Patent [19]

Holloway et al.

[11] Patent Number: 4,772,631

[45] Date of Patent: Sep. 20, 1988

[54] PHENYL ETHERS

[75] Inventors: Brian R. Holloway, Congleton; Ralph Howe, Macclesfield; Balbir S. Rao, Holmes Chapel; Donald Stribling, Prestbury, all of England

[73] Assignee: Imperial Chemical Industries PlC, London, England

[21] Appl. No.: 889,857

[22] Filed: Jul. 28, 1986

[30] Foreign Application Priority Data

Jul. 30, 1985 [GB] United Kingdom ............... 8519154

[51] Int. Cl.$^4$ ............... A61K 31/235; C07C 69/736
[52] U.S. Cl. ............... 514/539; 514/567; 514/619; 514/652; 560/42; 562/451; 564/165; 564/349; 564/351; 260/501.1
[58] Field of Search ............... 560/42; 562/451; 564/349, 165, 351; 514/539, 567, 652, 646, 619; 260/501.1

[56] References Cited

U.S. PATENT DOCUMENTS

| | | | |
|---|---|---|---|
| 3,723,524 | 3/1973 | Augstein et al. | 260/559 S |
| 3,873,600 | 3/1975 | Brandstrom et al. | 560/42 |
| 4,146,638 | 3/1979 | Renth et al. | 562/451 |
| 4,191,765 | 3/1980 | Fritsch et al. | 560/42 |
| 4,329,358 | 5/1982 | Ainsworth et al. | 560/42 |
| 4,338,333 | 7/1982 | Ainsworth et al. | 560/42 |

FOREIGN PATENT DOCUMENTS

| | | |
|---|---|---|
| 0007294 | 1/1980 | European Pat. Off. . |
| 0064487 | 11/1982 | European Pat. Off. . |
| 164700 | 12/1985 | European Pat. Off. ............ 560/42 |
| 1957706 | 5/1970 | Fed. Rep. of Germany . |
| 1159072 | 12/1983 | Canada ................ 560/42 |
| 84/8004 | 4/1985 | South Africa . |
| 632987 | 11/1982 | Switzerland . |
| 1245148 | 9/1971 | United Kingdom . |
| 1589838 | 4/1981 | United Kingdom . |

OTHER PUBLICATIONS

Carlsson et al I, *Chemical Abstracts*, vol. 98, No. 106954c (1983).
Carlsson et al II, *Chemical Abstracts*, vol. 98, No. 137626b (1983).
Carlsson et al III, *Chemical Abstracts*, vol. 89, No. 129247c (1978).
Ainsworth et al, *Chemical Abstracts*, vol. 104, No. 224720p (1986).
Duckworth et al, *Chemical Abstracts*, vol. 104, No. 224722r (1986).

Primary Examiner—James H. Reamer
Assistant Examiner—Bruce D. Gray
Attorney, Agent, or Firm—Cushman, Darby & Cushman

[57] ABSTRACT

The invention concerns a series of novel phenoxyacetic acid ethers (and pharmaceutically acceptable salts thereof) of the formula I in which $R^1$ is H or F, $R^2$ and $R^3$ are H or (1-3C)alkyl, Z is $CH_2OH$ or a group $—CO.R^4$ in which $R^4$ is OH, $NH_2$ or (1-6C)alkoxy. The invention also includes pharmaceutical compositions for use in treating obesity and related conditions and provides processes for the manufacture of the novel ethers.

10 Claims, No Drawings

PHENYL ETHERS

The invention concerns novel phenyl ethers, and, more particularly, novel ethers containing a (2-hydroxy-3-phenoxypropyl)amino group, which ethers stimulate thermogenesis in warm-blooded animals and are of use in the treatment of obesity and related conditions, such as obesity in mature onset diabetics. The invention also provides pharmaceutical compositions for use in the administration of the phenyl ethers of the invention to warm-blooded animals and processes for the manufacture of the novel phenyl ethers.

In European patent application, publication No. 140243 there is described a series of phenoxyacetic acid derivatives which are said to be of value in treating obesity. We have now discovered (and this is a basis for the present invention) that, surprisingly, certain novel ethers of the formula I defined below, which differ from the compounds of the art in having an oxygen link interposed between the alkylene chain and the phenoxyacetic acid moiety, possess significant thermogenic properties at doses which causes relatively little cardiac stimulation, it being understood that selectivity of thermogenic effect is an important requirement for a useful agent in the treatment of, for example, obesity and related conditions.

According to the invention there is provided a phenoxyacetic acid derivative of the formula I [set out hereinafter together with the other chemical formulae identified by Roman numerals] wherein $R^1$ is hydrogen or fluoro; $R^2$ and $R^3$ are independently selected from hydrogen and (1–3C)alkyl; and Z is hydroxymethyl or a group of the formula —$CO.R^4$ in which $R^4$ is hydroxy, (1–6C)alkoxy or amino; or a pharmaceutically acceptable salt thereof as appropriate.

It will be appreciated that the compounds of formula I contain one or two asymmetric carbon atoms and can exist as optically active enantiomers or as optically inactive racemates. The present invention encompasses any enantiomer, racemate and/or (when two asymmetric carbon atoms are present) diastereoisomer, which possesses thermogenic properties in warm-blooded animals, it being well known in the chemical art how to prepare individual enantiomers, for example by resolution of the racemate or by stereospecific synthesis, and how to determine the thermogenic properties, for example, using the standard tests described hereinafter.

The group —$OCH_2Z$ is generally located in the meta- or para-position relative to thee oxyethylamino side-chain, of which positions the para-position is preferred.

A preferred value for $R^1$ is hydrogen.

A particular value for $R^2$ or $R^3$ is, for example, hydrogen, methyl, ethyl or propyl, of which values, hydrogen or methyl are generally preferred.

A particular value for $R^4$ when it is (1–6C)-alkoxy is, for example, methoxy, ethoxy, butoxy or t-butoxy.

A preferred value for Z is a group of the formula —$CO.R^4$.

Preferred values for $R^4$ include hydroxy, amino, methoxy and t-butoxy.

Typical compounds of formula I are set out in the accompanying Examples and, of these, that described in Example 1 is of particular interest, and is provided, together with its pharmaceutically acceptable acid-addition salts, as a further feature of the invention.

A preferred group of compounds of the invention comprises those compounds of formula I wherein $R^1$ is hydrogen, $R^2$ is hydrogen or methyl, $R^3$ is hydrogen, Z is a group of the formula —$CO.R^5$ in which $R^5$ is hydroxy, (1–4C)alkoxy (such as methoxy, ethoxy or t-butoxy) or is amino, and the groups —$OCH_2Z$ and —$OCH_2CR^2R^3NH$— are attached in para relationship, together with the pharmaceutically acceptable salts thereof, as appropriate.

The compounds of formula I are basic and may be isolated and used either in the form of the free base or of a pharmaceutically acceptable acid-addition salt thereof. In addition, those compounds of formula I wherein $R^4$ (or $R^5$) is hydroxy are amphoteric and may be isolated and used in the zwitterionic form, or as a pharmaceutically acceptable acid-addition salt, or as a salt with a base affording a pharmaceutically acceptable cation.

Particular examples of pharmaceutically acceptable acid-addition salts include, for example, salts with inorganic acids such as hydrohalides (especially hydrochlorides or hydrobromides), sulphates and phosphates, and salts with organic acids such as succinates, citrates, lactates, tartrates, oxalates and salts derived from acidic polymeric resins, such as the free acid form of sulphonated polystyrene.

Particular examples of salts with bases affording a pharmaceutically acceptable cation include, for example, alkali metal and alkaline earth metal salts, such as sodium, potassium, calcium and magnesium salts, and ammonium salts and salts with suitable organic bases, such as triethanolamine.

The novel compounds of formula I may be obtained by conventional processes of organic chemistry well known in the art for the production of structurally analogous compounds, for example as set out in our UK patent specification, Ser. No. 1,455,116. Such processes are provided as a further feature of the invention and are illustrated by the following procedures in which $R^1$, $R^2$, $R^3$, $R^4$, and Z have any of the previously defined meanings:

(a) A phenol derivative of the formula II is reacted with an alkylating agent of the formula $X.CH_2Z$ wherein X is a suitable leaving group, for example a chloro, bromo, iodo, methanesulphonyloxy or p-toluenesulphonyloxy group.

The process is conveniently performed in the presence of an external base, for example an inorganic base such as an alkali metal carbonate or acetate (e.g. potassium carbonate or sodium acetate), or an alkali metal hydride (e.g. sodium hydride), and at a temperature in the range, for example, 10° to 120° C. A suitable solvent or diluent, for example acetone, methyl ethyl ketone, propan-2-ol, 1,2-dimethoxyethane or t-butyl methyl ether may conveniently be used. In order to minimise side-reactions, the process may also be carried out by pre-reacting the phenol of formula II with a suitable base to form the corresponding salt which is added to the alkylating agent of the formula $X.CH_2Z$.

The starting phenol derivatives of formula II may be obtained by conventional procedures of organic chemistry. Thus, for example, they may be obtained by reaction of a phenol of the formula III with an epoxide of the formula IV in a suitable solvent or diluent, for example, an alcohol such as ethanol or propan-2-ol, at a temperature in the range, for example, 10° to 110° C. and conveniently at or near the boiling point of the reaction mixture. The epoxides of formula IV are known per se but can be made by reaction of phenol or o-fluorophenol with epichlorohydrin or epibromohydrin in the presence of a suitable base such as an alkali metal hydroxide, piperidine, morpholine or N-methylmorpholine, in a suitable solvent or diluent such as methanol, ethanol or propan-2-ol, conveniently at or near the boiling point of the reaction mixture.

In general, it is preferred to react the epoxide of formula IV with a protected phenol derivative of formula V wherein Q is a suitable protecting group such as benzyl. In this case, following the reaction of compounds IV and V, the protecting group is removed, for example in the case of benzyl by hydrogenolysis, for example using hydrogenation at a pressure in the range, for example, 3 to 30 bar in the presence of a palladium-on-carbon catalyst in an inert diluent or solvent for example, a (1-4C)alkanol (such as methanol, ethanol or t-butyl alcohol) and at a temperature of, for example, 20°-80° C.

It is to be understood that the epoxides of formulae IV may be used in their racemic or enantiomeric forms.

(b) An amine derivative of the formula VI is reacted with an epoxide of formula IV.

It will be appreciated that this reaction is a modification of the procedure described above for the production of the starting materials of formula II and that, therefore, generally similar reaction conditionss may be employed.

The necessary starting materials of formula VI may be made from the corresponding phenols of formula III by reaction with a compound of the formula $X.CH_2Z$ as defined above using analogous reaction conditions to those described above in process (a).

(c) A protected derivative of the formula VII wherein Q is a suitable protecting group is deprotected.

A suitable protecting group is, for example, a hydrogenolysable group such as benzyl, 4-methoxybenzyl or 3,4-dimethoxybenzyl, which may be removed, for example by hydrogenation using conditions similar to those defined above in the production of the starting materials for process (a). Hydrogen pressure of, for example, 3 to 30 bar may be used at a temperature in the general range, for example, 20° to 80° C.

The protected derivatives of formula VII may be obtained by using process (a) or (b) with appropriate starting materials in which the amino group is protected with a suitable protecting group. When Q is benzyl, the corresponding benzylated starting materials analogous to those of formula VI may conveniently be obtained, for example, by reductive alkylation of the compounds of formula VI with benzaldehyde in the presence of sodium borohydride in a solvent or diluent such as methanol at 0° to 25° C.

(d) For a compound wherein Z is carboxy, an ester or amide of the formula I in which Z is replaced by a radical of the formula $-CO.R^6$, wherein $R^6$ is amino, (1-6C)alkoxy, phenoxy or benzyloxy, is decomposed.

A preferred decomposition method is hydrolysis using acid or base conditions. Suitable acid conditions are, for example a strong mineral acid such as hydrochloric, sulphuric or phosphoric acid, conveniently at a temperature in the range, for example, 20° to 110° C. and in a polar solvent, such as water, a (1-4C)alkanol (for example methanol or ethanol) or acetic acid. In such cases, the corresponding mineral acid salt of the compound of formula I wherein Z is carboxy may be conveniently isolated. Alternatively, base conditions may be used, for example lithium, sodium or potassium hydroxide, conveniently in a suitable solvent or diluent such as an aqueous (1-4C)alkanol at a temperature in the range, for example, 10° to 110° C.

As yet further alternatives, when $R^6$ is t-butoxy, the decomposition may be carried out, for example, by thermolysis at a temperature in the range, for example, 100° to 220° C., alone or in the presence of a suitable diluent such as diphenyl ether; or, when $R^6$ is benzyloxy, by hydrogenolysis, for example as described hereinbefore for process (c).

(e) For a compound wherein Z is carbamoyl, an ester of the formula I in which Z is replaced by a radical of the formula $-CO.R^7$ wherein $R^7$ is (1-6C)alkoxy, phenoxy or benzyloxy is reacted with ammonia.

The process is generally performed in a suitable inert solvent or diluent, for example, a (1-4C)alkanol such as methanol or ethanol and at a temperature in the range, for example, 0° to 60° C., optionally in a pressure vessel to prevent loss of ammonia.

The necessary starting esters are either compounds of the invention or may be obtained by analogy with the compounds of the invention using an analogous process to (a), (b) or (c) herein.

(f) For a compound wherein Z is hydroxymethyl, the corresponding acid of formula I wherein Z is carboxy or an ester of the formula I in which Z is replaced by a radical of the formula $-COR^7$ as defined in (e) above, is reduced.

Suitable reducing conditions are any of those known in the art to reduce carboxylic acids or esters to the corresponding hydroxymethyl derivatives. For example, an aluminium or boron hydride derivative such as lithium aluminium hydride, sodium borohydride, sodium cyanoborohydride or sodium dihydro-bis(2-methoxyethoxy)aluminate, or an alternative alkali metal salt, may be used.

The process is conveniently carried out in a suitable solvent or diluent, for example, in a (1-4C)alkanol or an ether, such as methanol, ethanol, tetrahydrofuran, 1,2-dimethoxyethane or t-butyl methyl ether, optionally together with a hydrocarbon such as toluene or xylene. The process is generally performed at the lowest temperature within the range, for example −15° to 80° C., which is consistent with a reasonable reaction rate.

(g) For a compound of formula I wherein one of $R^2$ and $R^3$ is hydrogen or (1-3C)alkyl and the other of $R^2$ and $R^3$ is hydrogen, an imine of the formula VIII where $R^8$ is hydrogen or (1-3C)alkyl is reduced.

The reduction may be carried out using any reagent known to reduce azomethine groups without affecting other reactive groupings such as the $CO.R^4$ group when present. For example, hydrogen may be used in the presence of a suitable catalyst, such as a platinum catalyst, and in a suitable solvent or diluent, such as a (1-4C)alkanol, optionally together with water and at a temperature in the range, for example, 10° to 30° C. Alternatively, for example, an alkali metal cyanoborohydride, such as sodium cyanoborohydride, may be used in a suitable solvent or diluent, such as acetonitrile, methanol, ethanol or propan-2-ol, and at a temperature in the range, for example, −20° to 30° C. When an alkali metal cyanoborohydride is used the reaction may be conveniently carried out at a pH of about 4, for example in the presence of acetic acid.

The imines of formula VIII may be conveniently obtained by condensation of an amine of the formula IX with a ketone derivative of the formula X in which $R^8$ has the meaning defined above. The condensation may be carried out using any known standard procedure, for example by removal of water by azeotropic distillation in a suitable solvent, such as toluene. In some cases, it may be convenient to carry out the condensation reaction forming the imine and the subsequent reduction in situ, for example by reacting an amine of the formula IX with a ketone derivative of the formula X as defined above (or a hydrate or hermiacetal thereof when $R^8$ is hydrogen) with an alkali metal borohydride or cyanoborohydride, and such a modified process is also provided by the invention.

Whereafter a compound of formula I wherein Z is carboxy may, if desired, be converted to the corresponding compound of formula I wherein Z is carbamoyl or [(1-6C)alkoxy]carbonyl by a conventional amidification or esterification procedure. Similarly, a compound of formula I wherein Z is hydroxymethyl may, if desired, be oxidised to the corresponding acid of formula I wherein Z is carboxy by conventional oxidation procedure, for example using platinum and oxygen in aqueous acetone or tetrahydrofuran, at a temperature in the range, for example, 10° to 50° C.

Whereafter, when a pharmaceutically acceptable salt is required, the compound of formula I in free base form (or, when $R^4$ is hydroxy, in zwitterionic form) is reacted with the appropriate acid or base using a conventional procedure. For example, when a hydrogen halide salt is required, it may conveniently be obtained by hydrogenation of the free base together with the stoichiometric amount of the corresponding benzyl halide.

Whereafter, when an enantiomer is required, the corresponding racemate may be resolved, for example by reaction with a suitable optically active acid using a conventional procedure.

Certain of the intermediates, for example those of formula II, are believed to be novel and are provided as further features of the invention.

As stated above, the compounds of formula I possess thermogenic properties and are of use in the treatment of obesity and/or related diseases of metabolic dysfunction, such as diabetes metllitus especially of adult onset. In addition, in some cases, the compounds of formula I may be of value in modification of carcass composition, for example, by increased catabolism of fat in meat producing animals, such as cattle, pigs, sheep, goats and/or rabbits.

The thermogenic effects of compounds of formula I may be demonstrated using the following standard tests:

(a) Rats are cold adapted by being placed in a cold environment (4° C.) for 10 days in order to increase their capacity for thermogenesis. They are then transferred to a thermoneutral environment (29° C.). Three hours later the core temperature is measured to determine a base-line reading and the test compound is administered subcutaneously or orally as a solution or suspension in 0.45% w/v aqueous sodium chloride, 0.25% w/v Polysorbate 80. After one hour, the core temperature is again measured. In this test, a compound which causes a statistically significant increase in the core temperature of >0.3° C. at a dose of 15 mg/kg or less is considered to be significantly active. This test acts as a model for the depressed thermogenesis which occurs during dieting.

(b) Rats are cold adapted at 4° C. for 4 days to increase their capacity for thermogenesis. They are then transferred to a warm environment of 23° C. for 2 days. On the following day, a test compound is administered subcutaneously or orally as described in (a). Animals are sacrificed one hour later and the interscapular, brown adipose tissue (BAT) pad is removed. BAT mitochondria are prepared by differential centrifugation and GDP binding is determined (Holloway et al., *International Journal Of Obesity*, 1984, 8, 295) as a measure of thermogenic activation. Each test includes a control which is dosed with the solution/suspension vehicle only and a positive control which is dosed with isoprenaline (as its sulphate) at 1 mg/kg. Test compounds are routinely dosed at 0.1, 1.0 and 10 mg/kg and results expressed in terms of the effect on GDP binding produced by isoprenaline. From these results, a dose ($ED_{50}$) necessary to produce 50% of the isoprenaline effect is calculated by linear regression analysis. Compounds are considered active in this test if they cause a significant elevation in GDP binding as compared to controls. This test serves to indicate that the thermogenic effects observed in test (a) are mediated through an increase in effect on BAT rather than by some non-specific or toxic mechanism.

(c) Rats are adapted to a thermoneutral environment (29° C.) for 2 weeks in order to decrease their capacity for BAT mediated non-shivering thermogenesis. During the final 3 days the animals are accustomed to use an apparatus for measuring heart rate non-invasively via foot-pad electrodes connected to an ECG integrator giving a continuous read-out of heart rate. A test compound is administered sub-cutaneously at the $ED_{50}$ determined in test (b), and heart rate is determined after 15 minutes. The procedure is then repeated in subsequent tests using increasing multiples of the $ED_{50}$ determined in test (b) until the heart rate (HR) reaches or exceeds 500 beats per minute, allowing the dose necessary to produce a heart rate of 500 beat per minute ($D_{500}$ dose) to be calculated.

The ratio of $D_{500}$ to $ED_{50}$ in test (b) is known as the selectivity index (SI) and provides a measure of the selectivity of the compound for BAT as opposed to the cardiovascular system. Compounds are considered to have significant selectivity which have an SI of >1. Non-selective compounds have an SI of <1 (for example isoprenaline=0.06).

In the above tests, the compounds of formula I in general produce effects of the following order without producing overt toxicity:

test (a): increase in core temperature of >0.5° C. following a sub-cutaneous dosage of <15 mg/kg;

test (b): sub-cutaneous $ED_{50}$ for GDP binding in BAT mitochondria of 0.01-10 mg/kg; and test (c): show an SI of >50.

By way of illustration, the compound described in the accompanying Example 1, produced the following effects in the above tests:

(a) 1.4° C. (at 10 mg/kg sub-cut.)
(b) sub-cutaneous $ED_{50}$: 0.428 mg/kg;
(c) $D_{500}$: 42.8 mg/kg; SI 100.

When used to produce thermogenic effects in warm-blooded animals including man, a compound of formula I, or a pharmaceutically acceptable salt thereof as appropriate, will be administered so that a dose in the general range 0.002-20 mg/kg, and preferably in the range 0.02-10 mg/kg, is admininstered daily, given in a single dose or divided doses as necessary. However, it will be appreciated by those skilled in the art that dosage will necessarily be varied as appropriate, depending on the severity of the condition under treatment and on the age and sex of the patient and according to known medical principles.

The compounds of formula I will generally be used for medical (or veterinary) purposes in the form of pharmaceutical compositions comprising a compound of formula I, or a pharmaceutically (or veterinarily) acceptable salt thereof as appropriate, as the active ingredient together with a pharmaceutically (or veterinarily) acceptable diluent or carrier. Such compositions are included in the invention and will typically be adapted for oral administration (including tablets, capsules, pills, powders, solutions, suspensions and the like) or parenteral administration (including sterile solutions, suspensions and emulsions). Compositions adapted for oral administration are generally preferred.

The compositions may be obtained using standard excipients and procedures well known in the art. However, in general wet granulation techniques and the use of higher alcohols during formulation should be avoided in order to minimise the possibility of interaction with the —$OCH_2Z$ group. A unit dose form such as a tablet or capsule will usually contain, for example 0.1–250 mg of active ingredient. The compositions may also contain other active ingredients known for use in the treatment of obesity and related conditions, for example appetite suppressants, vitamins and hypoglycaemic agents.

The invention will now be illustrated by the following Examples in which, unless otherwise stated:

(a) all operations were carried out at room temperature that is at a temperature in the range 18°–26° C.;

(b) evaporations were performed under reduced pressure on a rotary evaporator;

(c) chromatography was carried out on Merck Kieselgel (Art 7734) obtained from E Merck, Darmstadt, Federal Republic of Germany;

(d) yields are for illustration only and are not to be interpreted as the maximum attainable by diligent process development; and (e) nuclear magnetic resonance (NMR) spectra were determined at 200 MHz in $d_6$-DMSO as solvent using tetramethylsilane (TMS) an internal standard and are expressed in delta values (parts per million) for protons relative to TMS, using conventional abbreviations to describe signal types.

EXAMPLE 1

A mixture of N-benzyl-N-(2-p-hydroxyphenoxyethyl)-2-hydroxy-3-phenoxypropylamine (4.0 g), methyl bromoacetate (1.56 g), anhydrous potassium carbonate (1.7 g) and potassium iodide (0.05 g) was stirred under reflux in dry acetone (50 ml) for 24 hours. The reaction mixture was cooled, solid removed by filtration and solvent evaporated. The residue of methyl 2-p-(2-[N-benzyl-(2-hydroxy-3-phenoxypropyl)amino]ethoxy)-phenoxyacetate was dissolved in methanol (90 ml) and acetic acid (30 ml). The solution obtained was hydrogenated in the presence of 10% w/w palladium-on-carbon (0.4 g) at about 20 bar and 60° C. for 48 hours. The mixture was cooled, solid removed by filtration and solvent evaporated. The residual oil was dissolved in methanol and treated with a solution of ether saturated with hydrogen chloride. The precipitated solid was crystallised twice from methanol to give methyl 2-p-(2-[(2-hydroxy-3-phenoxypropyl)amino]ethoxy)phenoxyacetate hydrochloride, 0.22 g, mp 170° C.; microanalysis: found C, 58.2; H, 6.3; N, 3.6; Cl, 8.8%; required for $C_{20}H_{26}NClO_6$: C, 58.3; H, 6.3; N, 3.4; Cl, 8.6%; NMR: 3.08 (dd, 1H, CHC$\underline{H_2}$NH), 3.26 (dd, 1H, CHC$\underline{H_2}$NH), 3.36 (t, 2H, NHC$\underline{H_2}$CH$_2$), 3.7 (s, 3H, CO$_2$CH$_3$), 4.0(d, 2H, OCH$_2$CH), 4.25(m, 3H, OC$\underline{H_2}$.CHOH—), 4.74 (s, 2H, OC$\underline{H_2}$CO), 6.8–7.05 (m, 7 aromatic H), 7.31 (m, 2 aromatic H).

The starting material was obtained as follows:

(a) A stirred mixture of 2-p-hydroxyphenoxyethylamine (4.0 g) and benzaldehyde (5.0 g) in methanol (50 ml) was cooled with ice and sodium borohydride (2.0 g) was added in portions over one hour. After stirring for a further 18 hours the solvent was evaporated. The residue was partitioned between 2M hydrochloric acid (200 ml) and ethyl acetate (100 ml). The acid layer was separated, made alkaline with potassium carbonate and then extracted with ethyl acetate. The extracts were dried (MgSO$_4$) and evaporated. The residual oil was dissolved in ethyl acetate and dry hydrogen chloride was passed through the solution until no further solid precipitated. The precipitate was collected and recrystallised from methanol and ethyl acetate to give N-benzyl-2-p-hydroxyphenoxyethylamine hydrochloride *, 2.3 g, mp 182°–184° C.

*The starting N-benzyl-2-p-hydroxyphenylethylamine hydrochloride may also be obtained as follows:
A mixture of p-(2-bromoethoxy)phenol (2.2 g), benzylamine (1.07 g) and triethylamine (1.01 g) in ethanol (30 ml) was heated under reflux for 18 hours. The solvent was evaporated and the residue was partitioned between 2M hydrochloric acid (100 ml) and ethyl acetate (50 ml). The acid layer was separated, made alkaline with potassium carbonate and then extracted with ethyl acetate. The extracts were dried (MgSO$_4$) and the solvent was evaporated. The residual oil was dissolved in ethyl acetate. Dry hydrogen chloride was then passed through the solution until no further solid precipitated. The solid was collected by filtration and recrystallised from a mixture of methanol and ethyl acetate to give N-benzyl-2-p-hydroxyphenoxyethylamine hydrochloride, 0.9 g, mp 182°–184° C.

(b) N-Benzyl-2-p-hydroxyphenoxyethylamine hydrochloride (3.5 g) was shaken with 1M sodium hydroxide solution (20 ml) and dichloromethane (20 ml). The organic layer was separated and washed with water (10 ml), dried (MgSO$_4$) and the solvent evaporated to give N-benzyl-2-p-hydroxyphenoxyethylamine as an oil.

(c) A mixture of N-benzyl-2-p-hydroxyphenoxyethylamine (2.5 g) and 1,2-epoxy-3-phenoxypropane (1.54 g) in propan-2-ol (50 ml) was heated under reflux for 72 hours. The solvent was removed by evaporation to give N-benzyl-N-(2-p-hydroxyphenoxyethyl)-2-hydroxy-3-phenoxypropylamine as an oil which was essentially pure as indicated by thin layer chromatography (TLC) [using silica plates and 5% methanol in dichloromethane as eluant] and was used without purification.

EXAMPLE 2

A mixture of methyl 2-p-(2-[(2-hydroxy-3-phenoxypropyl)amino]ethoxy)phenoxyacetate, (0.92 g), (−)-di-p-toluoyltartaric acid monohydrate (0.991 g) in methanol (15 ml) was evaporated by boiling to give a final volume of 5 ml. Methyl acetate (10 ml) was added and the mixture was again concentrated to 5 ml volume. This treatment was repeated once more. The mixture was left at ambient temperature for 18 hours. The solid which had formed was collected and crystallised from methanol and methyl acetate to give (−)-methyl 2-p-(2-[(2-hydroxy-3-phenoxypropyl)amino]ethoxy)phenoxyacetate (−)-di-p-toluoyltartrate, (0.337 g); mp 146°–148° C.; $^{25}[\alpha]_D = -80.3°$ (C=0.97; methanol).

(−)-Methyl 2-p-(2-[(2-hydroxy-3-phenoxypropyl)amino]ethoxy)phenoxyacetate (−)-di-p-toluoyltartrate (0.33 g) was partitioned between 5% w/v sodium hydrogen carbonate solution (10 ml) and dichloromethane (10 ml). The organic layer was separated, dried (MgSO$_4$) and the solvent was evaporated. The residual solid, (0.148 g), mp 114°–116° C., $^{23}[\alpha]_D = -7.8°$ (C=0.97; dichloromethane), was dissolved in methyl acetate. Dry hydrogen chloride gas was passed through the solution until no further solid precipitated. The precipitate was collected and crystallised from methanol and methyl acetate to give (−)-methyl 2-p-(2-[(2-hydroxy-3-phenoxypropyl)amino]ethoxy)phenoxyacetate hydrochloride, (0.092 g), mp 156°–157° C., $^{23}[\alpha]_D = -12.1°$ (C=1.0; methanol).

EXAMPLE 3

A mixture of N-benzyl-N-(2-p-hydroxyphenoxyethyl)-3-o-fluorophenoxy-2-hydroxypropylamine (5.4 g), methyl bromoacetate (2.0 g), anhydrous potassium carbonate (1.79) and potassium iodide (0.05 g) was stirred under reflux in dry acetone (80 ml) for 24 hours. The reaction mixture was cooled, solid removed by filtration and the solvent evaporated. The residue was dissolved in dichloromethane (40 ml) and washed successively with 10% w/v sodium bicarbonate solution (20 ml) and water (20 ml), then dried (MgSO$_4$) and the solvent removed by evaporation. The oil (6.18 g) obtained was purified by chromatography on silica, eluting with 1% v/v methanol in dichloromethane to give methyl 2-p-(2-[N-benzyl-(3-o-fluorophenoxy-2-hydroxypropyl)amino]ethoxy)phenoxyacetate as a colourless oil. This was dissolved in methanol (100 ml) and stirred with decolourising charcoal (1 g) for 1 hour. The charcoal was removed by filtration and the filtrate was hydrogenated in the presence of benzyl chloride (0.71 g) and 10% w/w palladium-on-carbon for 2 hours at atmospheric pressure. The catalyst was removed by filtration and the solvent was evaporated from the filtrate. The residual solid was crystallised twice from a mixture of methanol and anhydrous ether to give methyl 2-p-(2-[(3-o-fluorophenoxy-2-hydroxypropyl)amino]ethoxy)-phenoxyacetate hydrochloride (0.55 g), mp 120°–122° C.; microanalysis, found: C, 55,7; H, 5.9; N, 3.2; Cl, 8.3%; required for C$_{20}$H$_{25}$NClFO$_6$: C, 55.9; H, 5.9; N, 3.3; Cl, 8.2%; NMR: 3.1 (dd, 1H, CHCH$_2$NH), 3.27 (m under HOD peak, 1H, CH.CH$_2$NH), 3.41 (t, 2H, NHCH$_2$CH$_2$), 3.68 (s, 3H, CO$_2$CH$_3$), 4.05 (d, 2H, OCH$_2$CH), 4.25 (d+m, 3H, OCH$_2$, CHOH), 4.71, (s, 2H, OCH$_2$CO), 5.93 (d, 1H, CHOH), 6.8–7.0 (m, 5 aromatic H), 7.1–7.3 (m, 3 aromatic H), 9.12 (broad s, 2H, NH$_2$+).

The starting material was obtained as follows:

A mixture of N-benzyl-2-p-hydroxyphenoxyethylamine hydrochloride (5.6 g), 1,2-epoxy-3-o-fluorophenoxypropane (3.6 g) and anhydrous potassium carbonate (2.7 g) was heated under reflux in propan-2-ol (100 ml) for 24 hours. The reaction mixture was cooled, the solid removed by filtration and the solvent evaporated from the filtrate. The residual oil was purified by chromatography on silica eluting with 1% v/v methanol in dichloromethane to give N-benzyl-N-(2-p-hydroxyphenoxyethyl)-3-o-fluorophenoxy-2-hydroxypropylamine as a colourless oil; NMR: 2.27–3.15 (m, 4H, CH$_2$NCH$_2$), 3.8 (dd, 2H, NCH$_2$Ph), 3.9–4.2 (m, 5H, OCH$_2$.CHOH, o-F-Ph.OCH$_2$), 6.7 (s, 4 aromatic H), 6.8–7.1 (m, 4 aromatic H), 7.3 (m, 5H, CH$_2$Ph).

EXAMPLE 4

A mixture of methyl p-(2-oxopropoxy)phenoxyacetate (15.3 g) and 2-hydroxy-3-phenoxypropylamine (10.75 g) in dry toluene (250 ml) was stirred under reflux for 18 hours in an apparatus for azeotropic distillation of water. The solvent was evaporated and the residual oil (formula VIII R$^1$=H; R$^8$=CH$_3$; OCH$_2$Z=p-OCH$_2$CO$_2$CH$_3$) was dissolved in methanol (150 ml). This solution was added to a pre-reduced suspension of Adam's catalyst (0.25 g) in methanol (100 ml) and the subsequent mixture was hydrogenated at atmospheric pressure for six hours. The catalyst was removed by filtration and the filtrate was concentrated in vacuo. The residual oil was purified by chromatography on silica using 1% v/v methanol in dichloromethane as eluant. The solid obtained was recrystallised repeatedly from methyl acetate to give methyl 2-p-(2-[(2-hydroxy-3-phenoxypropyl)amino]propoxy)-phenoxyacetate (U) (2.88 g), mp 115°–116° C. microanalysis, found: C, 64.9; H, 7.1; N, 3.6; required for C$_{21}$H$_{27}$NO$_6$: C, 64.8; H, 6.9; N, 3.6% NMR (400 MHz): 1.17 (2d, 3H, CHCH$_3$), 2.82 (m, 1H, NHCH$_2$), 2.95 (m, 1H, NHCH$_2$), 3.11 (dd, 1H, CHCH$_3$), 3.8 (s, 3H, COOCH$_3$), 3.80 (m, 1H, OCH$_2$CH$_3$), 3.88 (m, 1H, OCH$_2$CH$_3$), 4.0 (m, 3H, OCH$_2$CHOH), 4.58 (m, 2H, OCH$_2$.CO), 6.8–7.0 (m, 7 aromatic H), 7.28 (m, 2 aromatic H) [Note: the presence of 2 doublets at 1.17 indicates the presence of both possible diastereoisomeric forms (A,B) of U, as an approximately 50:50 mixture, based on measurement of the two doublet of doublet signals at 3.11 delta; each diastereoisomeric form is racemic and comprises a pair of opposite optical enantiomers].

The mixture of diastereoisomeric forms of compound U was separated as follows:

(i) The above 50:50 mixture of U (2.8 g) was dissolved in methanol (20 ml) and a solution of anhydrous oxalic acid (0.65 g) in methanol (20 ml) was then added. The solvent was removed by evaporation and the residue was crystallised from methanol to give one diastereoisomeric form of the compound U as its oxalate salt, mp 191°–192°. This salt was partitioned between 10M sodium hydroxide (0.5 ml), brine (20 ml) and dichloromethane (40 ml). The organic layer was dried (MgSO$_4$) and the solvent was removed by evaporation. The residue was crystallised from methyl acetate to give diastereoisomeric form A of the compound U as the solid free base (0.53 g), mp 103.5°–105.5° C., analytically pure by microanalysis and of >95% isomeric purity (based on the presence of only one doublet of doublets in the 400 MHz NMR spectrum at 3.11 delta).

(ii) The mother liquors from the methanol recrystallisation step of the oxalate salt of U in (i) were evaporated. The residual solid was then fractionally crystallised from methyl acetate to give a second oxalate salt, mp 125°–127° C. This salt was converted to the free base form as described in (i). The residual solid obtained was crystallised twice from a mixture of methanol and methyl acetate to give the free base form of compound U as a mixture of the two diastereoisomers A and B (0.15 g), mp 116°–117° C., microanalytically pure and containing approximately 25% of diastereoisomer A and 75% of diastereoisomer B, (based on 400 MHz NMR measurement of the two doublets of doublets at 3.11 delta).

EXAMPLE 5

Using a similar procedure to that described in Example 1, but starting from N-benzyl-N-(2-m-hydroxyphenoxyethyl)-2-hydroxy-3-phenoxypropylamine (1.6 g), methyl bromoacetate (0.58 g), anhydrous potassium carbonate (0.6 g) and potassium iodide (0.05 g) in acetone (80 ml), and with intermediate isolation of methyl 2-m-(2-[N-benzyl-(2-hydroxy-3-phenoxypropyl)amino]ethoxy)phenoxyacetate (1.1 g), there was obtained methyl 2-m-(2-[(2-hydroxy-3-phenoxypropyl- )amino]ethoxy)phenoxyacetate hydrochloride (0.35 g), mp 164°–167° C.; microanalysis, found: C, 58.0; H, 6.5; N, 3.3; Cl, 8.7%; required for $C_{20}H_{26}NClO_6$; C, 58.3; H, 6.4; N, 3.4; Cl, 8.6%; NMR: 3.1 (dd, 1H, CHC$\underline{H}_2$NH), 3.25 (dd, 1H, CHC$\underline{H}_2$NH), 3.4 (t, 2H, NHC$\underline{H}_2$C$\overline{H}_2$), 3.7 (s, 3H, CO$_2$CH$_3$), 3.9–4.1 (m, 2H, OC$\underline{H}_2$C$\overline{H}$), 4.2–4.4 (m, 3H, OC$\underline{H}_2$.C$\underline{H}$OH—), 4.78 (s, 2H, $\overline{OCH_2}$CO), 5.98 (d, 1H, CH$\overline{OH}$), 6.5–6.7 (m, 3 aromatic H), 6.9–7.0 (m, 3 aromatic $\overline{H}$), 7.1–7.4 (m, 3 aromatic H), 9.1 (s, 2H, NH$_2^+$).

The starting material was obtained as follows:

(a) A mixture of resorcinol (88 g), 1,2-dibromoethane (180 g) and potassium hydroxide (44.8 g) was stirred under reflux in methanol (600 ml) for 24 hours. The reaction mixture was cooled. The residual solid was removed by filtration and the filtrate was evaporated to give 3-(2-bromoethoxy)phenol as an oil which was essentially pure as indicated by thin layer chromatography (tlc) [using silica plates and 10% v/v methanol in dichloromethane as eluant] and was used without purification.

(b) A mixture of 3-(2-bromoethoxy)phenol (40 g) and benzylamine (39.2 g) was stirred under reflux in ethanol (800 ml) for 18 hours. The reaction mixture was cooled and the solvent evaporated. The residual oil was dissolved in ethyl acetate (200 ml). The solution was washed with 2M hydrochloric acid (100 ml). The aqueous layer was basified with solid potassium carbonate and extracted with ether (2×100 ml). The extracts were washed successively with water (50 ml) and brine (50 ml), and were then dried (MgSO$_4$). The dry ethereal solution was treated with a solution of ether saturated with hydrogen chloride. The precipitated solid was crystallised twice from a mixture of methanol/ethyl acetate to give N-benzyl-2-(m-hydroxyphenoxy)ethylamine hydrochloride (19.2 g), mp 148°–149° C.; NMR: 3.2 (t, 2H, C$\underline{H}_2$NH), 4.22 (s+t, 4H, C$\underline{H}_2$O, NC$\underline{H}_2$Ph), 6.4 (m, 3 aromatic H), 7.1 (t, 1 aromatic H), 7.3–7.8 (m, 5 aromatic H).

(c) A mixture of N-benzyl-2-(m-hydroxyphenoxy)ethylamine hydrochloride (2.79 g), 1,2-epoxy-3-phenoxypropane (1.5 g) and anhydrous potassium carbonate (2.0 g) was heated under reflux in propan-2-ol for 18 hours. The reaction mixture was cooled and the solvent was evaporated to give N-benzyl-N-(2-m-hydroxyphenoxyethyl)-2-hydroxy-3-phenoxypropylamine as an oil, which was essentially pure as indicated by tlc [using silica plates and 5% methanol in dichloromethane as eluant] and was used without purification.

EXAMPLE 6

A suspension of methyl 2-p-(2-[(2-hydroxy-3-phenoxypropyl)amino]ethoxy)phenoxyacetate hydrochloride (0.015 g) in 2M hydrochloric acid (1 ml) was heated at 95°–100° C. for 30 minutes. The clear solution obtained was allowed to cool to ambient temperature, giving 2-p-(2-[(2-hydroxy-3-phenoxypropyl)amino]ethoxy)-phenoxyacetic acid hydrochloride (0.011 g), mp 180°–182° C.

EXAMPLE 7

A mixture of methyl 2-p-(2-[(2-hydroxy-3-phenoxypropyl)amino]ethoxy)phenoxyacetate hydrochloride (0.507 g) and sodium hydroxide (100 mg) in methanol (5 ml) and water (15 ml) was heated at 95°–100° C. for 18 hours. The methanol was removed by distillation and the pH of the residual layer was adjusted to 6 with 2M hydrochloric acid. An oil was deposited which slowly solidified. The solid was crystallised from water to give 2-p-(2-[(2-hydroxy-3-phenoxypropyl)amino]ethoxy)-phenoxyacetic acid, mp 186°–188° C.; microanalysis, found: C, 62.2; H, 6.2; N, 3.5; H$_2$O, 0.9%; required for $C_{19}H_{23}NO_6 \cdot \frac{1}{4}H_2O$: C, 62.4; H, 6.5; N, 3.8; H$_2$O, 1.2%.

EXAMPLE 8

A solution of methyl 2-p-(2-[(2-hydroxy-3-phenoxypropyl)amino]ethoxy)phenoxyacetate hydrochloride (0.3 g) in methanol (30 ml) was saturated with ammonia and kept at ambient temperature for 24 hours. The solid which deposited was collected and crystallised from methanol to give 2-p-(2-[(2-hydroxy-3-phenoxypropyl)amino]ethoxy)phenoxyacetamide (0.08 g), mp 142°–144° C.; microanalysis: found C, 63.1; H, 6.8; N, 7.5%; required for $C_{19}H_{24}N_2O_5$: C, 63.3; H, 6.7; N, 7.8%. The methanolic filtrate from the above procedure was concentrated to half its volume by distilling out solvent. On cooling, the residual liquor gave further solid which was recrystallised from methanol to give 2-p-(2-[(2-hydroxy-3-phenoxypropyl)amino]ethoxy)-phenoxyacetamide hydrochloride (0.12 g), mp 222°–223° C.; microanalysis: found: C, 57.4; H, 6.3; N, 6.9; Cl, 8.7%; required for $C_{19}H_{25}N_2ClO_5$: C, 57.5; H, 6.3; N, 7.1; Cl, 8.9%.

EXAMPLE 9

A solution of 2-p-(2-[(2-hydroxy-3-phenoxypropyl)amino]ethoxy)phenoxyacetamide (0.5 g) in 2M hydrochloric acid (10 ml) was heated at 95°–100° C. for 4 hours. The hot solution was filtered and allowed to cool to give 2-p-(2-[(2-hydroxy-3-phenoxypropyl)amino]ethoxy)phenoxyacetic acid hydrochloride (0.26 g), mp 179°–181° C.; microanalysis; found: C, 57.3; H, 6.2; N, 3.5; Cl, 8.9%; required for $C_{19}H_{24}NClO_6$: C, 57.3; H, 6.0; N, 3.5; Cl, 8.9%.

EXAMPLE 10

Sodium borohydride (1.0 g) was added in small portions over 30 minutes to a solution of methyl 2-p-(2-[(2-hydroxy-3-phenoxypropyl)amino]ethoxy)phenoxyacetate hydrochloride, (0.6 g) in methanol (30 ml). After the addition was complete, the mixture was heated under reflux for 2 hours. The solution was cooled and the solvent evaporated. The residue which was obtained was partitioned between water (30 ml) and dichloromethane (30 ml). The organic layer was separated, dried (MgSO$_4$) and the solvent evaporated. The residue was crystallised from ethyl acetate to give 2-[2-p-(2-[(2-hydroxy-3-phenoxypropyl)amino]ethoxy)-phenoxy]ethanol (0.26 g), mp 99°–101° C.; microanalysis: found C, 65.5; H, 7.3; N, 4.0%; required for $C_{19}H_{25}NO_5$; C, 65.7; H, 7.2; N, 4.0%.

EXAMPLE 11

Methyl 2-p-(2-[(2-hydroxy-3-phenoxypropyl)amino]ethoxy)phenoxyacetate hydrochloride (1.9 g) was partitioned between 5% w/v sodium hydrogen carbonate solution (50 ml) and dichloromethane (50 ml). The organic layer was dried (MgSO$_4$) and the solvent evaporated. The residual solid was crystallised from methanol to give methyl 2-p-(2-[(2-hydroxy-3-phenoxypropyl)amino]ethoxy)phenoxyacetate (1.67 g), mp 116°–117.5° C.; microanalysis, found: C, 64.0; H, 6.7; N, 3.7%; required for $C_{20}H_{25}NO_6$: C, 64.0; H, 6.7; N, 3.7%.

EXAMPLE 12

A mixture of N-benzyl-N-(2-p-hydroxyphenoxyethyl)-2-hydroxy-3-phenoxypropylamine (3.22 g), t-butyl bromoacetate (1.6 g), anhydrous potassium carbonate (1.13 g) and potassium iodide (0.02 g) was stirred under reflux in dry acetone (150 ml) for 72 hours. The reaction mixture was cooled. The residual solid was removed by filtration and the filtrate was evaporated. The residue of t-butyl 2-p-(2-[N-benzyl-(2-hydroxy-3-phenoxypropyl)amino]ethoxy)phenoxyacetate was dissolved in t-butyl alcohol (70 ml) and acetic acid (30 ml). The solution obtained was hydrogenated in the presence of 10% w/w palladium-on-carbon (0.4 g) at about 20 bar and 60° C. for 48 hours. The mixture was cooled and the catalyst was separated by filtration. The filtrate was evaporated to give an oil (2.8 g) which was purified by chromatography on silica, eluting with 10% v/v t-butyl alcohol in dichloromethane to give t-butyl 2-p-(2-[(2-hydroxy-3-phenoxypropyl)amino]ethoxy)-phenoxyacetate (0.25 g), mp 74°-76° C. [after recrystallisation from ether/petroleum ether (b.p. 60°-80° C.)]; microanalysis: found C, 66.2; H, 7.7; N, 3.3%; required for $C_{23}H_{31}NO_6$: C, 66.2; H, 7.4; N3.4%; NMR (CDCl$_3$): 1.50 (s, 9H, But), 2.30 (s, 2H, OH, NH), 2.80-3.10 (m, 4H, CH$_2$NCH$_2$), 4.02 (m, 5H, OCH$_2$CH(OH), OCH$_2$CH$_2$), 4.48 (s, 2H, OCH$_2$CO), 6.90 (m, 7 aromatic H), 7.25 (m, 2 aromatic H).

EXAMPLE 13

A mixture of methyl 2-p-(2-aminoethoxy)phenoxyacetate hydrochloride (0.164 g), triethylamine (0.063 g) and 1,2-epoxy-3-phenoxypropane (0.094 g) was heated under reflux in methanol (10 ml) for 24 hours. The reaction mixture was cooled and the solvent evaporated. The residue was partitioned between 5% w/v sodium hydrogen carbonate solution (10 ml) and dichloromethane (20 ml). The organic layer was separated, dried (MgSO$_4$) and the solvent evaporated. The residue was purified by chromatography on silica, eluting with 5% v/v methanol in dichloromethane, to give methyl 2-p-(2-[(2-hydroxy-3-phenoxypropyl)amino]ethoxy)-phenoxyacetate as an oil. This was dissolved in methyl acetate and dry hydrogen chloride was passed through the solution until no further solid separated. The solid was collected and washed with methyl acetate to give methyl 2-p-(2-[(2-hydroxy-3-phenoxypropyl)amino]ethoxy)phenoxyacetate hydrochloride, (0.015 g), essentially identical with that obtained in Example 1.

The necessary starting material was obtained as follows:

(i) Sodium hydride (0.34 g of a 60% w/w suspension in mineral oil) was added to N-benzyl-2-p-hydroxyphenoxyethylamine (1.2 g) dissolved in dry dimethylformamide (DMF) (50 ml). The resulting suspension was stirred for approximately 15 minutes until a clear solution was obtained. Methyl bromoacetate (0.76 g) was added and the mixture was stirred for 4 hours. It was then poured into water (150 ml) and extracted with dichloromethane (2×100 ml). The extracts were washed successively with water (2×50 ml) and brine (50 ml), then dried (MgSO$_4$) and the solvent evaporated. The residue was dissolved in ether and dry hydrogen chloride was passed through the solution until no further solid precipitated. The precipitate was collected and recrystallised from methanol and ether to give methyl 2-p-(2-[benzylamino]ethoxy)phenoxyacetate hydrochloride (0.42 g) mp, 178° C.

(ii) A solution of methyl 2-p-(2-[benzylamino]ethoxy)phenoxyacetate hydrochloride (1.7 g) in methanol (30 ml) and acetic acid (10 ml) was hydrogenated in the presence of 10% w/w palladium-on-carbon (0.1 g) at about 20 bar and 60° C. for 48 hours. The mixture was cooled. The catalyst was removed by filtration and the filtrate was evaporated. The residual oil was dissolved in methanol and treated with a solution of ether saturated with hydrogen chloride. The precipitated solid was crystallised from methanol and methyl acetate to give methyl 2-p-(2-aminoethoxy)phenoxyacetate hydrochloride (0.24 g), mp 175° C.

EXAMPLE 14

Sodium hydride (30 mg of a 60% w/w dispersion in mineral oil) was added to a solution of p-(2-[(2-hydroxy-3-phenoxypropyl)amino]ethoxy)phenol (240 mg) in DMF (10 ml) at 0°-10° C. under an atmosphere of argon. The resulting suspension was stirred for about 15 minutes until a clear solution was obtained. Methyl bromoacetate (0.8 ml) was then added, and the mixture stirred for 18 hours under an atmosphere of argon. It was then poured into water (50 ml) and extracted with dichloromethane (3×20 ml). The extracts were washed successively with water (2×20 ml) and brine (20 ml), then dried (MgSO$_4$) and the solvent evaporated.

The residue was dissolved in methyl acetate and dry hydrogen chloride was passed through the solution until no further solid deposited. The solid was collected and washed with methyl acetate to give methyl 2-p-(2-[(2-hydroxy-3-phenoxypropyl)amino]ethoxy)phenoxyacetate hydrochloride (0.12 g), essentially identical to that isolated in Example 1. [Note: the above procedure may alternatively be carried out using potassium carbonate in acetone containing a catalytic amount of potassium iodide, in place of sodium hydride in DMF, for example using the reaction conditions and work up procedure described in Example 1.]

The starting phenol derivative was obtained as follows:

A mixture of p-(2-aminoethoxy)phenol hydrochloride, (1.89 g) triethylamine (1.01 g) and 1,2-epoxy-3-phenoxy-propane (1.5 g) was heated under reflux for 24 hours. The reaction mixture was cooled and the solvent was evaporated. The residue was partitioned between dichloromethane (100 ml) and 10% w/v potassium carbonate solution. The organic layer was separated, dried (MgSO$_4$), and the solvent was evaporated. The residual oil was dissolved in ethyl acetate and dry hydrogen chloride was passed through the solution until no further solid precipitated. The precipitate was collected and recrystallised from methanol and ethyl acetate to give p-(2-[2-hydroxy-3-phenoxypropylamino]ethoxy)phenol hydrochloride (0.53 g) mp, 171° C.; microanalysis: found C, 60.3; H, 6.7; N, 4.0; Cl, 10.6%; required for $C_{17}H_{22}NClO_4$: C, 60.1; H, 6.5; N, 4.1; Cl, 10.5% NMR: 3.09 (dd, 1H, CHOH.CH$_2$NH), 3.28 (dd, 1H, CHOH.CH$_2$NH), 3.47 (t, 2H, NHCH$_2$CH$_2$), 4.15 (m, 2H, NHCH$_2$CH$_2$), 4.25 (m, 1H, CHOH), 5.01 (br s, 1H, CHOH), 6.67+6.79 (2d, 4 aromatic H), 6.92 (m, 3 aromatic H), 7.26 (t, 2 aromatic H), 9.1 (br s, NH$_2$+ +phenolic OH). [Note: p-(2-[(2-hydroxy-3-phenoxypropylamino]ethoxy)phenol in addition to being a valuable intermediate also shows significant thermogenic properties in its own right (sub-cut.ED$_{50}$ in test (b): 0.51 mg/kg; SI in test (c) >100) and is provided together with its pharmaceutically acceptable salts, and compositions, as a further feature of the invention.]

EXAMPLE 15

As stated previously, suitable pharmaceutical compositions of compounds of formula I defined hereinbefore may be obtained by standard formulation techniques. However, in general, when Z is an alkoxycarbonyl (such as methoxycarbonyl) wet granulation techniques or procedures involving the use of alkanols not corresponding to the alkoxy group of the compound, are preferably avoided.

A typical tablet formulation suitable for oral administration to warm-blooded animals comprises as active ingredient a micronised form of a compound of formula I, or a pharmaceutically acceptable salt thereof, as defined hereinbefore, and may be produced by direct compression together with micronised lactose containing a standard disintegrant and/or lubricant. When tablets containing small amounts of active ingredient (for example 0.5–10 mg) are required, the active ingredient may be micronised together with lactose in the ratio of 1:10 parts by weight and then this material is diluted with further lactose or microcrysalline cellulose containing 0.5% by weight of a lubricant (such as magnesium stearate) and 5% by weight of a disintegrant (such as cross-linked sodium carboxymethyl cellulose or sodium starch glycolate).

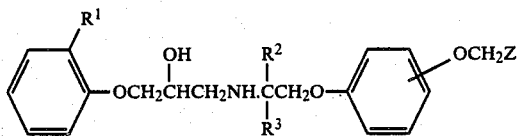  I

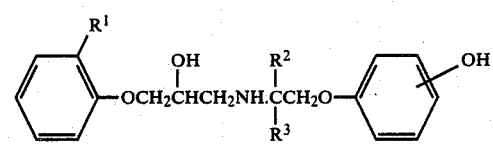  II

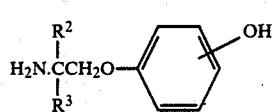  III

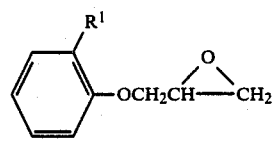  IV

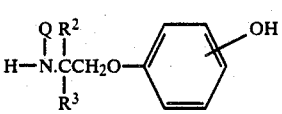  V

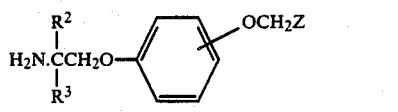  VI

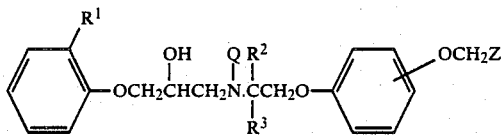  VII

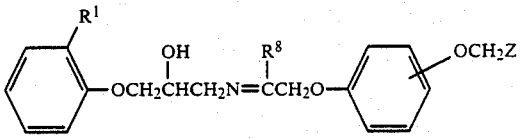  VIII

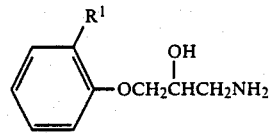  IX

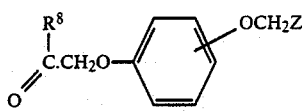  X

What we claim is:

1. A phenoxyacetic acid derivative of the formula

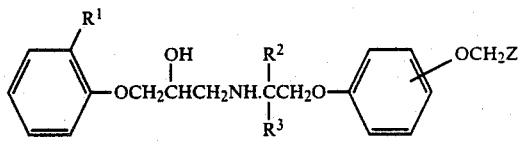

wherein $R^1$ is hydrogen or fluoro; $R^2$ and $R^3$ are independently selected from hydrogen and (1–3C)alkyl; and Z is hydroxymethyl or a group of the formula —$CO.R^4$ in which $R^4$ is hydroxy, (1–6C)alkoxy or amino; or a pharmaceutically acceptable salt thereof.

2. A compound as claimed in claim 1 wherein $R^2$ and $R^3$ are independently selected from hydrogen, methyl, ethyl and propyl, and $R^4$ is hydroxy, amino, methoxy, ethoxy, butoxy or t-butoxy.

3. A compound as claimed in claim 1 or 2 wherein the group —$OCH_2Z$ is located in the meta- or para-position relative to the oxyethylamino side-chain.

4. A compound as claimed in claim 1 wherein $R^2$ and $R^3$ are independently hydrogen or methyl.

5. A compound as claimed in claim 1 or 4 wherein $R^1$ is hydrogen and Z is a group of the formula —$CO.R^4$ and the group —$OCH_2Z$ is located in the para-position relative to the oxyethylamino side-chain.

6. A compound of the formula

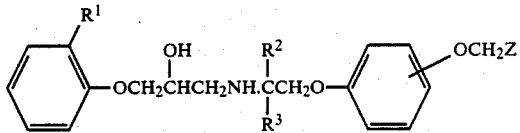

wherein $R^1$ is hydrogen, $R^2$ is hydrogen, $R^3$ is hydrogen, Z is a group of the formula —$CO.R^5$ in which $R^5$ is hydroxy, (1–4C)alkoxy or amino, and the groups —$OCH_2Z$ and —$OCH_2CR^2R^3NH$— are attached in para-relationship, together with the pharmaceutically acceptable salts thereof.

7. A compound selected from 2-p-(2-[(2-hydroxy-3-phenoxypropyl)amino]ethoxy)phenoxyacetic acid, its methyl ester, and the pharmaceutically acceptable salts of said acid or ester.

8. A pharmaceutically acceptable salt as claimed in claim 1, which is a pharmaceutically acceptable acid-addition salt with an inorganic or organic acid, or, when Z is a carboxy group, a salt with an inorganic or organic base affording a pharmaceutically acceptable cation.

9. A pharmaceutical composition which comprises a phenoxyacetic acid derivative of the formula

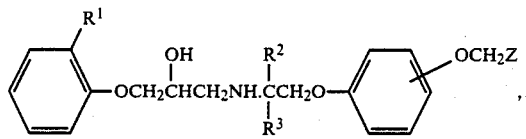

or a pharmaceutically acceptable salt thereof, as defined in claim 1, together with a pharmaceutically acceptable diluent or carrier.

10. A method for the production of a thermogenic effect in a warm-blooded animal requiring such treatment which comprises administering to said animal an effective amount of a compound of the formula

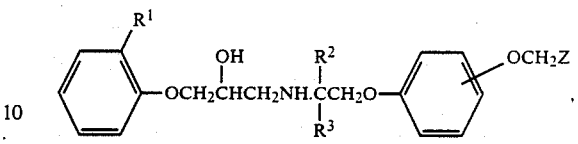

or a pharmaceutically acceptable salt thereof, as claimed in claim 1.

* * * * *